United States Patent [19]

Shroot et al.

[11] Patent Number: 4,677,123

[45] Date of Patent: Jun. 30, 1987

[54] PHARMACEUTICAL AND COSMETIC COMPOSITIONS CONTAINING AS AN ACTIVE INGREDIENT 1,8-DIHYDROXY-10-PHENYL-9-ANTHRONE AND A PROCESS FOR PREPARATION THEREOF

[75] Inventors: Braham Shroot, Antibes; Gérard Lang, Epinay-sur-Seine; Jean Maignan, Tremblay les Gonesse, all of France

[73] Assignee: Centre International de Recherches Dermatologiques C.I.R.D., Valbonne, France

[21] Appl. No.: 753,906

[22] Filed: Jul. 11, 1985

[30] Foreign Application Priority Data

Jul. 12, 1984 [FR] France .................. 84 11075

[51] Int. Cl.$^4$ ............................................ A61K 31/12
[52] U.S. Cl. ..................................................... 514/680
[58] Field of Search ........................................ 514/680

[56] References Cited

PUBLICATIONS

Chemical Abstracts 63: 4219g, (1965).

*Primary Examiner*—Jerome D. Goldberg
*Attorney, Agent, or Firm*—Cushman, Darby & Cushman

[57] ABSTRACT

Pharmaceutical or cosmetic composition containing as the active component 1,8-dihydroxy-10-phenyl-9-anthrone, and a process for preparing said active component.

2 Claims, No Drawings

PHARMACEUTICAL AND COSMETIC COMPOSITIONS CONTAINING AS AN ACTIVE INGREDIENT 1,8-DIHYDROXY-10-PHENYL-9-ANTHRONE AND A PROCESS FOR PREPARATION THEREOF

The present invention relates to new cosmetic or pharmaceutical compositions containing, as the active component, 1,8-dihydroxy-10-phenyl-9-anthrone.

The present invention also relates to a process for preparing this compound.

1,8-dihydroxy-10-phenyl-9-anthrone is a compound disclosed in an article by O. E. Schuetz and H. H. Schultze-Mosgau, Archiv der Pharmazie 298, 273–281 (1965).

1,8-dihydroxy-10-phenyl-9-anthrone has the formula

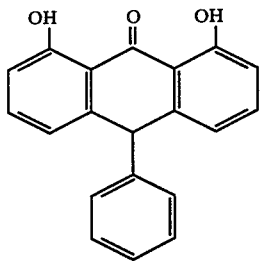

When prepared according to the process of the present invention, this compound is provided in the form of a crystallized solid having a melting point of 193°–194° C., although in the above-mentioned article, the melting point of this compound is indicated as being 290° C.

The process of the present invention comprises reacting phenyl lithium with 1,8-dihydroxy anthraquinone in the presence of an anhydrous organic solvent, such as tetrahydrofuran, to form 1,8,10-trihydroxy-10-phenyl-9-anthrone which is then reduced with a reducing agent so as to produce 1,8-dihydroxy-10-phenyl-9-anthrone.

The reducing agent can be, for example, a stannous salt, or a metal such as tin or zinc.

It has now been discovered that this compound, i.e. 1,8-dihydroxy-10-phenyl-9-anthrone, possesses cytostatic and anti-inflammatory properties thereby making it useful in cosmetology and principally for use in body and hair hygiene. This compound is also useful in human or veterinary medicine. principally as an antiproliferative agent in the treatment of psoriasis and warts, and as an anti-inflammatory agent in the treatment of rheumatism, dermatosis, eczema, seborrheic or pellicular poll evil and sunburn.

The present invention also relates to new cosmetic and pharmaceutical compositions comprising, as the active component, 1,8-dihydroxy-10-phenyl-9-anthrone.

These compositions contain the active component in combination with a carrier suitable for enteral, topical or parenteral administration.

In these compositions, the concentration of the active component generally ranges from 0.01 to 70% by weight, the concentration generally being a function principally of the manner of administration or application.

The pharmaceutical compositions administered enterally or parenterally can be provided in the form of tablets, granules, gels, capsules, syrups, drinkable suspension, ingestible powders, or even in the form of injectable solution or suspensions.

For topical administration, the compositions of the present invention can be provided in the form of ointments, unguents, tinctures, solution, lotions, creams, gels, sprays, suspensions, micronized powders or shampoos. These compositions can also contain inert or pharmacologically active adjuvants such as, for example, binders, fillers, diluents, thickening agents, preservatives and the like.

These pharmaceutical forms of the compositions of the present invention are prepared in accordance with conventional procedures.

The posology varies principally as a function of the disorder being treated and the form of administration employed.

For enteral or parenteral administration the active component is administered in an amount ranging from 0.005 to 5 g each day to an adult, in one or more doses.

For topical application, depending upon the therapeutic or cosmetic effect sought, there is applied, for example, on the areas of the skin to be treated, 1 to 5 g of a composition containing 0.01 to 5 g of the active component per 100 g of composition.

Because of the antiproliferative and anti-inflammatory properties of the compound of formula I, the composition of the present invention can be used principally in the treatment of eczema, psoriasis, dermatosis, seborrheic or pellicular poll evil, sunburns and rheumatism.

The present invention also relates to a packaged medicine prepared industrially, said medicine comprising a pharmaceutical composition such as defined above, in an appropriate container, said container having affixed thereto a label identifying the manner of administration for the treatment of disorders involving an inflammatory condition or abnormal cellular proliferations.

The present invention also relates to the use of the compound of formula I in an industrially prepared packaged medicine, such as defined above.

The following non-limiting examples illustrate the present invention. In these examples the active component is referred to as compound of formula I or compound I and has been prepared in accordance with procedures set out below.

PREPARATION OF THE COMPOUND OF FORMULA I (a) Preparation of 10-phenyl-1,8-10-trihydroxy-9-anthrone In a two liter reactor fitted with a mechanical stirrer, an argon lead-in tube, a condenser and an introduction funnel, there are introduced 30 g of 1,8-dihydroxy anthraquinone and 2 liters of anhydrous tetrahydrofuran. The solution obtained is then cooled to −70° C.

At this temperature, the anthraquinone is crystallized. There is then added, with stirring, over a 30 minute period a solution which contains 4 equivalents of phenyl lithium.

The temperature of the reaction mixture is maintained throughout the addition between −60° and −70° C. At the end of the addition, a check is made on withdrawn samples to assure that all the 1,8-dihydroxy anthraquinone is transformed. At this same temperature, the reaction mixture is acidified by adding 400 cm³ of acetic acid. Thereafter the reaction mixture is permitted to return to ambient temperature. The solvent is evaporated to dryness under reduced pressure and the resulting product, which is in the form of an oily mass, crystallizes by stirring in water.

The resulting crystals are filtered, washed with dichloromethane and then dried, yielding 32 g of yellow crystals which are then recrystallized in methanol. The product has a melting point of 216° C.

Analysis: $C_{20}H_{14}O_4$: Calculated: C: 75.46; H: 4.43; O: 20.10; Found: 75.48; 4.35; 19.95

(b) Preparation of 1,8-dihydroxy-10-phenyl-9-anthrone

In a 2 liter reactor fitted with a mechanical stirrer, and an argon lead-in tube, there are introduced 50 g of 10-phenyl-1,8,10-trihydroxy-9-anthrone, and then 200 g of crushed stannous chloride and 2 liters of acetic acid.

To this mixture, stirred at ambient temperature, there are slowly added, over a 30 minute period 200 cm³ of concentrated HCl. The disappearance of the 10-phenyl-1,8,10-trihydroxy-9-anthrone is followed by thin layer chromatography. After about 2 hours, the reduction reaction is terminated. The 1,8-dihydroxy-10-phenyl-9-anthrone which precipitates in the medium is filtered, washed with water and dried, yielding 42 g of light yellow crystals. The filtrate is poured on a mixture of 1 liter of water and 1 kg of crushed ice. The remainder of the product precipitates and is then filtered, washed with water and dried, thus providing an additional quantity of 4 g of the expected product.

The 1,8-dihydroxy-10-phenyl-9-anthrone thus obtained is pure.

It has a melting point of 193°-194° C.

Analysis: $C_{20}H_{14}O_3$: Calculated: C: 79.45; H: 4.66; O: 15.87; Found: 79.25; 4.71; 16.00

The structure of the 1,8-dihydroxy-10-phenyl-9-anthrone is confirmed by mass spectrography or one observes on the spectrum the relative peak at m/e: 302 by direct ionization and at m/e: 303 by chemical ionization with isobutane corresponding to $M+H^+$. These results are in accord with the molar mass of 302 g of product.

The NMR spectrum also confirms this structure. In particular a singulet is observed at 5.30 ppm whose integration corresponds to a proton. It is this which is linked to the carbon in the 10-position of the anthrone ring.

The signal of the eleven aromatic protons is a multiplet whose δ is from 6.60 to 7.50 ppm (11).

Finally, the spectrum exhibits another singulet at 12.40 ppm, which disappears by exchange with heavy water and whose integration corresponds well with the two protons of hydroxyl groups in the 1- and 8-positions.

Example 1

| Ointment (suspension) | |
|---|---|
| Compound I | 1.60 g |
| Petrolatum-Codex, sufficient amount for | 100.00 g |

Example 2

| Ointment removable with water (suspension) | |
|---|---|
| Compound I | 1.00 g |
| Polyethylene glycol 400 | 60.00 g |
| Polyethylene glycol 4000 | 25.00 g |
| Petrolatum oil | 100.00 g |

Example 3

| Non-ionic cream (water-in-oil suspension) | |
|---|---|
| Compound I | 1.50 g |
| Anhydrous eucerin (mixture of emulsified lanolin alcohols and waxes and refined oils based on hydro-carbons, sold by BDF Medical | 40.00 g |
| Preservative, sufficient amount | |
| Demineralized water, sufficient amount for | 100.00 g |

Example 4

| Anionic cream (oil-in-water suspension) | |
|---|---|
| Compound I | 1.50 g |
| Sodium dodecyl sulfate | 0.78 g |
| 1,2-propanediol | 1.56 g |
| Cetyl alcohol | 19.50 g |
| Thick petrolatum oil | 19.50 g |
| Preservative, sufficient amount | |
| Sterile demineralized water, sufficient amount for | 100.00 g |

Example 5

| Anhydrous hydrophobic gel | |
|---|---|
| Compound I | 1.000 g |
| Aerosil 200 (silica solid by Degussa) | 7.000 g |
| Isopropyl myristate, sufficient amount for | 100.00 g |

Example 6

| Gelled aqueous suspension | |
|---|---|
| Compound I | 0.10 g |
| Propylene glycol | 10.00 g |
| Hydroxypropyl cellulose | 2.00 g |
| Preservative, sufficient amount | |
| Sterile demineralized water, sufficient amount for | 100.00 g |

Example 7

| 0.8 g tablet | |
|---|---|
| Compound I | 0.500 g |
| Wheat starch | 0.205 g |
| Dicalcium phosphate | 0.040 g |
| Lactose | 0.040 g |
| Talc | 0.010 g |
| Magnesium stearate | 0.005 g |

Example 8

| 0.46 g gelule | |
|---|---|
| (a) powder formula | |
| Compound I | 0.30 g |
| Corn starch | 0.06 g |
| Magnesium stearate | 0.01 g |
| Sucrose, sufficient amount for | 0.46 g |
| (b) The above powder is packaged in a gelule made of gelatin and $TiO_2$. | |

Example 9

| Drinkable suspension in 10 ml ampoules | |
| --- | --- |
| Compound I | 0.10 g |
| Glycerine | 2.40 g |
| Sorbitol, 70% | 2.00 g |
| Sucrose | 0.10 g |
| Sodium parahydroxy benzoate | 0.08 g |
| Flavoring, sufficient amount | |
| Purified water, sufficient amount for | 10.00 ml |

Example 10

| Granules or pellets | |
| --- | --- |
| Compound I | 0.300 g |
| Sucrose | 1.680 g |
| Sodium alginate | 0.020 g |
| Purified water | 0.400 g |

The paste obtained by mixing these four components in granulated while wet, then dried and divided into 2 g packets.

Example 11

Study of Pharmacologic Properties (A) Study of anti-inflammatory activity—topical application.

This activity has been studied on rats in an edema test of the ear provoked by croton oil. The protocol is that described by G. Tonelli et al. Endocr. 77 625-634 (1965).

The compound studied was applied either in suspension in petrolatum, at a rate of 1.5% by weight of the active component, or in an oil-in-water cream of the following formulation:
- 1.5% of the compound of formula I
- 40% of anhydrous eucerin
- water, sufficient for 100%

There is applied in each case an amount of the composition corresponding to 1.5 mg of active component.

The results are as follows:

The application of the composition in petrolatum reduces the edema 36% relative to the non-treated control.

The application of the composition in the form of a cream reduces the edema 50% relative to the control.

(B) Cytostatic Activity

Th method used in that described by Jacques and Reichert, in the British Journal of Dermatology, 105, Supplement 20, pp 45-48, (1981). This method permits to study the diminution of the incorporation of tritiated thymidine in a culture of fibroblasts of human skin in increasing exponential phase.

The product studied is added to various increasing concentrations.

One determines the $K_{0.5}$ does which is the dose, expressed in micromoles/liter, necessary to diminish by 50%, relative to non-treated cultures, the incorporation of tritiated thymidine.

With the compound of formula I, it has been determined that the $K_{0.5}$ is 4 micromoles/liter.

Examples of Capillary Products with DT 198

Example 12

| Two part shampoo to be mixed at time of use | |
| --- | --- |
| (a) 7.5 g of the treating part, the composition of which is set forth below is packaged in self-breakable glass ampoules under an inert atmosphere. | |
| Formulation | |
| Compound I | 1.00 g |
| Dibutyl phthalate, sufficient amount for | 100.00 g |
| Other formulations | |
| (i) Compound I | 0.50 g |
| Butoxane M20, sufficient amount for | 100.00 g |
| (ii) Compound I | 0.50 g |
| Miglycol 812 (triglycerides of capric caprylic acids, sold by Dynamit Nobel), sufficient amount for | 100.00 g |
| (b) 22.5 g of the washing part, the composition of which is set forth below is packaged in a flexible flask provided with a cap stopper applicator. | |
| Dodecanediol polyglycidolated with 3.5 moles of glycidol, sold under the trade name NI 170 | 20.00 g |
| Condensate of $C_{16}$ epoxides on polyethylene glycol 3000 (in a 150/100 ratio), sold under the trade name DV 281 | 1.75 g |
| Citric acid, 50% in water, sufficient amount for pH = 3 | |
| NaOH (IM), sufficient amount for pH = 4.5 | |
| Water, sufficient amount for | 100.00 g |

This mixture is applied at the time of use to a wet scalp and is permitted to remain in contact therewith for 15 minutes. The shampoo is emulsified by adding water little by little. The hair and scalp are then rinsed abundantly with water.

Example 13

Pre-shampoo lotion 10 g of a pre-shampoo lotion, the composition of which is given below is packaged in self breakable glass ampoules under an inert atmosphere.

| Formulation | |
| --- | --- |
| Compound I | 0.10 g |
| Butoxane M20 (compound of Example 1 of French patent application 84 13253), sufficient amount for | 100.00 g |
| Other formulations | |
| (a) Compound I | 0.05 g |
| Miglyol 812, sufficient amount for | 100.00 g |
| (b) Compound I | 0.20 g |
| Isopropyl myristate, sufficient amount for | 100.00 g |

This lotion is applied stroke by stroke on a dry scalp and is permitted to remain in contact therewith for 15 minutes. The hair and scalp are then rinsed and the hair is washed with a suitable shampoo.

What is claimed is:

1. A method for combatting skin inflammation comprising administering to a person suffering from skin inflammation an effective amount of a pharmaceutical or cosmetic composition comprising in a pharmaceutically or cosmetically acceptable carrier, 1,8-dihydroxy-10-phenyl-9-anthrone, as an anti-inflammatory agent, present in an amount ranging from 0.01 to 70 percent by weight based on the total weight of said composition.

2. A method for the treatment of psoriasis or warts comprising administering to a person suffering from psoriasis or warts an effective amount of a pharmaceutical composition comprising in a pharmaceutically acceptable carrier, 1,8-dihydroxy-10-phenyl-9-anthrone, as an antiproliferative agent, present in an amount ranging from 0.01 to 70 percent by weight based on the total weight of said composition.

* * * * *